US005726301A

United States Patent [19]
Reddy et al.

[11] Patent Number: 5,726,301
[45] Date of Patent: Mar. 10, 1998

[54] CAC H-PHOSPHONATE AND ITS USE IN THE SYNTHESIS OF OLIGONUCLEOTIDES

[75] Inventors: M. Parameswara Reddy, Brea; Naeem B. Hanna, Fullerton; Firdous Farooqui, Brea, all of Calif.

[73] Assignee: Beckman Instruments, Inc., Fullerton, Calif.

[21] Appl. No.: 415,112

[22] Filed: Mar. 31, 1995

Related U.S. Application Data

[63] Continuation-in-part of Ser. No. 873,330, Apr. 24, 1992, Pat. No. 5,428,148.
[51] Int. Cl.$^6$ .......................... C07H 21/04; C07H 19/10
[52] U.S. Cl. ............... 536/25.34; 536/26.8; 536/28.51
[58] Field of Search ............................ 536/25.34, 26.8

[56] References Cited

U.S. PATENT DOCUMENTS 5,248,148  9/1993  Reddy et al. ............................ 536/26.8

FOREIGN PATENT DOCUMENTS 0723973  7/1996  European Pat. Off. .

OTHER PUBLICATIONS

Antkowiak et al., "Further Studies on Synthesis and Properties of the Protected Triester Nucleotides as a New Key Intermediate for the Synthesis of Oligoribonucleotides," in the *Third Symposium on the Chemistry of Nucleic Acid Components*, Oct. 8, 1975 at Lublice Castle, Czechoslovakia, published by Info Retrival. Ltd., Washington, D.C. in *Nucleic Acids Research, Special Publication No. 1*, pp. s133–s136 (1975).

Westman et al., "Improving the H-phosphonate Approach to Oligoribonucletide Synthesis," in the *21st Symposium on Nucleic Acids Chemistry* on Nov. 9, 1994 at Matsuyama, Japan, published by Oxford University Press (Oxford, England) in *Nucleic Acids Symposium Series* No. 31, pp. 25–26 (1994).

Zain et al., "Nucleoside H-Phosphonates. 15. Preparation of Nucleoside H-Phosphonate Monoesters from the Corresponding Nucleoside H-Phosphonates," *J. Organic Chem.* 60(25), 8241–8244 (1995).

Rozners et al., "Synthesis of RNA Fragments Using the H-Phosphonate Method and 2'(2-Chlorobenzoyl) Protection," from the *Proceedings of the Eleventh International Round Table on Nucleosides, Nucleotides and Their Biological Applications* at Leuven, Belgium on Sep. 7, 1994, published by Marcel Dekker, Inc. (New York, NY) in Nucleosides and Nucleotides, 14(3–5), 855–857 (1995).

Frauendorf, A et al; "Automated Synthesis, Structure and Biological Activity of Backbone–Modified Oligonucleotides. The Antisense Approach"; Studies in Natural Products Chemistry, vol. 13, 1993; pp. 257–294. Month of publication data is unavailable.

Dahl, O; "Preparation of Nucleoside Phosphorothioates, Phosphorodithioates and Related Compounds"; Sulfur Reports, vol. 11(1), 1991, pp. 167–193. Month of publication data is unavailable.

Shibahara, S.; et al; "Inhibition of Human Immunodeficiency virus (HIV–1) Replication by Synthetic Oligo–RNA Derivatives; Nucleic Acid Research"; vol. 17., pp. 239–253 (1989). Month of publication data is unavailable.

Froehler, B., et al; "Synthesis of DNA via Deoxynucleoside H–phosphonate Intermediates; Nucleic Acids Research"; vol. 14, No. 13, 1986; pp. 5399–5406. Month of publication data is unavailable.

Stein, C.A., et al; "Physicochemical Properties of Phosphorothioate Oligodeoxynucleotides"; Nucleic Acids Research; vol. 16, No. 8, 1988; pp. 3209–3221. Month of publication data is unavailable.

Seeberger, P.H., et al; "Oxidative Formation of Phosphorodithioates Via H–Phosphonodithioates"; Tetrahedron Letters, vol. 36, No. 5, 1995, 695–698. Month of publication data is unavailable.

Agrawal, S., et al; "Efficient Synthesis of Oligoribonucleotide and Its Phosphorothioate Analogue Using H–Phosphonate Approach"; Tetrahedron Letters, vol. 31, No. 52, 1990; pp. 7541–7544.

Brill, W.; "Thioalkylation of Nucleoside–H–Phosphonates and Its Application to Solid Phase Synthesis of Oligonucleotides"; Tetrahedron Letters, vol. 36, No. 5, 1995, pp. 703–706. Month of publication data is unavailable.

Garegg, P. J., et al; "Nucleoside Hydrogenphosphonates in Oligonucleotide Synthesis"; Chemica Scripta 26, 59 (1986). Month of publication data is unavailable.

Sakatsume, O., et al; "Use of New Phosphonylating and Coupling Agents in the Synthesis of Oligodeoxyribonucleotides via the H–phosphonate Approach"; Nucleic Acids Research, vol. 18, No. 11, pp. 3327–3331.

Jankowska, J., et al; "Studies on Aryl H–Phosphonates. I. An Efficient Method for the Preparation of Deoxyribo–and Ribonucleoside 3'–H–Phosphonate Monoesters by Transesterification of Diphenyl H–Phosphonate"; Tetrahedron Letters, vol. 35, No. 20, pp. 3355–3358 (1994). Month of publication data is unavailable.

(List continued on next page.)

*Primary Examiner*—John Kight
*Assistant Examiner*—L. Eric Crane
*Attorney, Agent, or Firm*—William H. May; P. R. Harder

[57] ABSTRACT

Disclosed herein are $N^4$ protected deoxycytidines for use in the synthesis of oligonucleotides, the protecting groups being represented by the formula: —CO—$(CH_2)_{0-9}$—$CH_3$. Preferred embodiments are $N^4$ acetyl deoxycytidines and include $N^4$ acetyl deoxycytidine phosphoramidites and $N^4$ acetyl deoxycytidine H-phosphonates. When used to prepare oligonucleotides the protected deoxycytidine compounds provide high quality oligonucleotide products with little side product from cleavage and deprotection reactions carried out with alkyl amine compounds.

9 Claims, 2 Drawing Sheets

OTHER PUBLICATIONS

Stawinski, J., et al; "Nucleoside H–Phosphonates. XI. A Convenient Method for the Preparation of Nucleoside H–Phosphonates"; Nucleosides & Nucleotides, 9(1), pp. 129–135 (1990). Month of publication data is unavailable.

Froehler, B.C., et al; "Nucleoside H–Phosphonates: Valuable Intermediates in the Synthesis of Deoxyoligonucleotides"; Tetrahedron Letters, vol. 27, No. 4, pp. 469–472 (1986). Month of publication data is unavailable.

Sakatsume, O., et al; "Use of New Phosphonylating and Coupling Agents in the Synthesis of Oligodeoxyribonucleotides Via The H–Phosphonate Approach"; Tetrahedron Letters, vol. 30, No. 46, pp. 6375–6378 (1989). Month of publication data is unavailable.

Tanaka, T.,et al; "Solid Phase Synthesis of Oligoribonucleotides Using the O–nitrobenzyl Group for 2'–hydroxyl Protection and H–phosphonate Chemistry"; Nucleic Acids Research, vol. 15, No. 18 pp. 7236–7248 (1987).

Andrus, A., et al; "2–Mercaptobenzopthiazole—An Improved Reagent for the Removal of Methylphosphate Protecting Groups From Oligodeoxynucleotide Phosphotriesters"; Tetrahedron Letters, vol. 29 No. 43, pp. 5479–5482, (1988).

Morvan, F., et al; "Modified Oligonucleotides: IV[1] Solid Phase Synthesis and Preliminary Evaluation of Phosphorothioate RNA as Potential Antisense Agents"; Tetrahedron Letters, vol. 31, No. 49, pp. 7149–7152 (1990). Month of publication data is unavailable.

Rozners, E., et al; "Synthesis of Oligoribonucleotides by the H–Phosphonate Approach Using Base Labile 2'–o–Protecting Groups. V. Recent Progress in Development of the Method"; Nucleosides & Nucleotides, 11(9), pp. 1579–1593 (1992). Month of publication data is unavailable.

Kung, Pei–Pei, et al; "H–Phosphonate DNA Synthesis Without Amino Protection"; Tetrahedron Letters, vol. 33, No. 40, pp. 5869–5872 (1992). Month of publication data is unavailable.

Komatsu, H., et al; "Synthesis of Protected 8–Substituted Deoxyribonucleosides and Its Helix Stability in Oligodeoxyribonucleotides Containing The Eco RI Recognition Site"; Nucleosides & Nucleotides, 11(1), pp. 85–95 (1992). Month of publication data is unavailable.

Sakatsume, O., et al; "Solid Phase Synthesis of Oligoribonucleotides Using the 1–[(2–chloro–4–methyl)phenyl]–4–methoxypiperidin–4–yl (Ctmp) Group for the Protection of the 2'–hydrox Functions and the H–Phosphonate Approach"; vol. 17, No. 10 (1989), pp. 3689–3697. Month of publication data is unavailable.

Porritt, G. M., et al; "Nucleoside Phosphonodithioates as Intermediates in the Preparation of Dinucleoside Phosphorodithioates and Phosphorothioates"; Tetrahedron Letters, vol. 30, No. 35, pp. 4713–4716 (1989). Month of publiction data is unavailable.

Iyer, R. P., et al; "The Automated Synthesis of Sulfur–Containing Oligodeoxyribonucleotides Using 3H–1, 2–Benzodithiol–3–One 1, 1–Dioxide as a Sulfur–Transfer Reagent"; J. Org. Chem. 1990, 55, pp 4693–4699. Month of publication data is unavailable.

Stawinski, J., et al; "3–H–2, 1–Benzoxathiol–3–one 1–oxide—A New Reagent for Stereospecific Oxidation of Nucleoside H–Phosphonothioate Diesters"; Tetrahedron Letters, vol. 33, No. 22, pp. 3189–3192, (1992). Month of publication data is unavailable.

Hosaka, H., et al; "A Convenient Approach to the Synthesis of Medium Size Deoxyribooligonucleotides by Improved New Phosphite Method"; Tetrahedron Letters, vol. 32, No. 6, pp. 785–788 (1991). Month of publication data is unavailable.

Adams, Steven P., et al; "Hindered Dialkylamino Nucleoside Phosphite Reagents in the Synthesis of Two DNA 51–Mers"; J. Am. Chem. Soc. 105 (1983), pp. 661–663, No. 3. Month of publication data is unavailable.

Stec, W. J., et al; "Bis(O,O–Diisopropoxy Phosphinothioyl) Disulfide—A Highly Efficient Sulfurizing Reagent for Cost–Effective Synthesis of Oligo (Nucleoside Phosphorothioate)s"; Tetrahedron Letters, vol. 34, No. 33, pp. 5317–5320 (1993). Month of publication data is unavailable.

SEQUENCE LISTING ( 1 ) GENERAL INFORMATION:

( i i i ) NUMBER OF SEQUENCES: 4

( 2 ) INFORMATION FOR SEQ ID NO: 1:

( i ) SEQUENCE CHARACTERISTICS:
        ( A ) LENGTH: 35 bases
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: no ( i v ) ANTI-SENSE: no ( x i ) SEQUENCE DESCRIPTION: SEQ ID NO:1:

CAG TGC AGC TCC TAG CAG CCT AGC GTA CTA GTC TT    35

( 2 ) INFORMATION FOR SEQ ID NO: 2:

( i ) SEQUENCE CHARACTERISTICS:
        ( A ) LENGTH: 51 bases
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: no ( i v ) ANTI-SENSE: no ( x i ) SEQUENCE DESCRIPTION: SEQ ID NO:2:

CAG TCC TAG TCA CAG TCC AGT CGC TCA AGC GTC CAG    36

TTG CAC AGG TCA CCT    51

( 2 ) INFORMATION FOR SEQ ID NO: 3:

( i ) SEQUENCE CHARACTERISTICS:
        ( A ) LENGTH: 101 bases
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: no ( i v ) ANTI-SENSE: no ( x i ) SEQUENCE DESCRIPTION: SEQ ID NO:3:

```
GCT GCC AGT TCG GTC ATC CGA TCC TCG GTC ACG CAA      36
CTG TCA ACG GCA CCT ACT CCT CGT AAC GTA GGA CAG      72
TCC GAT TCG CAC GTG CAA AGC CCA TTC AT              101
```

( 2 ) INFORMATION FOR SEQ ID NO: 4:

( i ) SEQUENCE CHARACTERISTICS:
        ( A ) LENGTH: 18 bases
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: no ( i v ) ANTI-SENSE: no ( x i ) SEQUENCE DESCRIPTION: SEQ ID NO:4:

```
CGC CAG GGT TTT CCC AGT                              18
```

CAC H-PHOSPHONATE AND ITS USE IN THE SYNTHESIS OF OLIGONUCLEOTIDES

RELATED APPLICATION

This application is related to U.S. Pat. No. 5,348,868 filed Apr. 24, 1992, issued Sep. 20, 1994, and entitled "Methods and Reagents for Cleaving and Deprotecting Oligonucleotides" by Parameswara Meda Reddy and Naeem Botros Hanna. The related patent is incorporated herein by reference.

This application is a continuation-in-part of U.S application Ser. No. 07/873,330 filed Apr. 24, 1992, and now U.S. Pat. No. 5,428,148, issued Jun. 27, 1995.

FIELD OF INVENTION

The present invention is generally directed to the synthesis of nucleic acids and in particular to reagents useful in the synthesis of nucleic acids. The reagents of the present invention have protecting groups which allow their fast cleavage and deprotection during the synthesis of nucleic acids.

BACKGROUND OF THE INVENTION

Deoxyribonucleic acid ("DNA") and ribonucleic acid ("RNA") are long, threadlike macromolecules, DNA comprising a chain of deoxyribonucleotides, and RNA comprising a chain of ribonucleotides. A nucleotide consists of a nucleoside and one or more phosphate groups; a nucleoside consists of a nitrogenous base linked to a pentose sugar. Typically, the phosphate group is attached to the fifth-carbon ("C-5") hydroxyl group ("OH") of the pentose sugar; however, it can also be attached to the third-carbon hydroxyl group ("C-3 OH"). In a molecule of DNA, the pentose sugar is deoxyribose, while in a molecule of RNA, the pentose sugar is ribose. The nitrogenous bases in DNA are adenine ("A"), cytosine ("C"), guanine ("G") and thymine ("T") . These bases are the same for RNA, except that uracil ("U") replaces thymine. Accordingly, the major nucleosides of DNA, collectively referred to as "deoxynucleosides", are as follows: deoxyadenosine ("dA"); deoxycytidine ("dC"); deoxyguanosine ("dG"); and thymidine ("T") . The corresponding ribonucleosides are designated "A"; "C"; "G"; and "U". (By convention, and because there is no corresponding thymidine ribonucleoside, deoxythymidine is typically designated as "T"; for consistency purposes, however, thymidine will be designated as "dT" throughout this disclosure).

The sequence of the nitrogenous bases of the DNA and RNA molecule encodes the genetic information contained in the molecule. The sugar and phosphate groups of a DNA or RNA molecule perform a structural role, forming the backbone of the molecule. Specifically, the sugar moiety of each nucleotide is linked to the sugar moiety of the adjacent nucleotide such that the 3'-hydroxyl of the pentose sugar of one nucleotide is linked to the 5'-hydroxyl of the pentose sugar of the adjacent nucleotide. The linkage between the two penrose sugars is typically via a phosphodiester bond. Based upon this linkage protocol, one end ("terminus") of the nucleotide chain has a 5'-terminus (e.g. hydroxyl, triphosphate, etc.), and the other end has a 3'-hydroxyl group. By convention, the base sequence of a nucleotide chain is written in a 5' to 3' direction, i.e., 5'-ATCG-3', or, simply ATCG.

While DNA and RNA are produced internally by living animals, DNA and RNA can be chemically synthesized such that synthetic strands of DNA and RNA can be rapidly and effectively produced. These strands are typically referred to as "synthetic oligonucleotides" or "oligonucleotides". A widely utilized chemical procedure for the synthesis of oligonucleotides is referred to as the "phosphoramidite methodology". See, e.g., U.S. Pat. No. 4,415,732; McBride, L. and Caruthers, M. *Tetrahedron Letters*, 24:245–248 (1983); and Sinha, N. et al. *Nucleic Acid Res*; 17:4539–4557 (1984), which are all incorporated herein by reference. Commercially available oligonucleotide synthesizers based upon the phosphoramidite methodology include, e.g., the Biosearch 8750™ and ABI 380B™, 392™ and 394™ DNA synthesizers.

The importance of chemically synthesized oligonucleotides is principally due to the wide variety of applications to which oligonucleotides can be directed. For example, oligonucleotides can be utilized in biological studies involving genetic engineering, recombinant DNA techniques, antisense DNA, detection of genomic DNA, probing DNA and RNA from various systems, detection of protein-DNA complexes, detection of site directed mutagenesis, primers for DNA and RNA synthesis, primers for amplification techniques such as the polymerase chain reaction, ligase chain reaction, etc. templates, linkers, and molecular interaction studies.

The primary structures of DNA and RNA molecules can be depicted as follows:

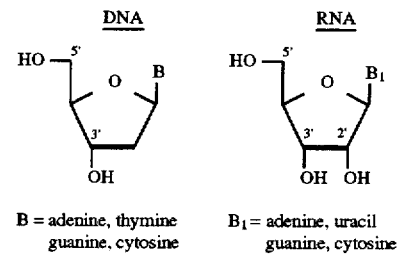

B = adenine, thymine guanine, cytosine $B_1$ = adenine, uracil guanine, cytosine The key step in nucleic acid synthesis is the specific and sequential formation of internucleotide phosphate linkages between a 5'-OH group of one nucleotide and a 3'-OH group of another nucleotide. Accordingly, in the typical synthesis of oligonucleotides, the phosphate group of an "incoming" nucleotide is combined with the 5'-OH group of another nucleotide (i.e. the 5'-OH group is "phosphorylated" or "phosphitylated"). These groups must be capable of actively participating in the synthesis of the otigonucleotide. Thus, the 5'-OH groups are modified (typically with a dimethoxy trityl ("DMT") group) such that an investigator can introduce two such nucleotides into a reaction chamber and adjust the conditions therein so that the two nucleotides are properly combined; by a series of successive such additions, a growing oligonucleotide having a defined sequence can be accurately generated.

The four bases of the nucleosides, adenine, thymine (uracil in the case of RNA), guanosine and cytosine, include moieties which are chemically reactive (e.g., exocyclic amino groups). These groups, unlike the 3'-OH and 5'-OH groups, must be "temporarily" protected, i.e. the protecting groups must be capable of blocking any reactive sites on the base until after the oligonucleotide synthesis is completed; after such synthesis is completed, these groups must also be capable of being removed from the bases such that the biological activity of the oligonucleotide is not affected.

The principal reason for temporarily protecting the base is that in the absence of such protecting groups, the exocyclic amino groups ("$NH_2$") of the bases can compete for binding to the 5'-OH group. If such a reaction takes place, the resulting product will not be useful. Accordingly, these protecting groups are important in reducing the occurrence of "side product formation" i.e. the formation of chemically similar, but unwanted, materials. Cytidine is particularly susceptible to side product formation during oligonucleotide cleavage and deprotection (i.e. the processes of removing an oligonucleotide from a solid support and removing such protecting groups, respectively). The most widely used protecting groups used in conjunction with the phosphoramidite methodologies for oligonucleotide synthesis are benzoyl for A and C, and isobutyryl for G and C. (thymine, which does not have an amino group, does not ordinarily require a protecting group). By convention, benzoyl is designated "bz", and isobutyryl is designated "ibu", such that the deoxynucleosides protected therewith are typically designated as follows: $dA^{bz}$; $dC^{bz}$; $dC^{ibu}$; and $dG^{ibu}$.

Benzoyl and isobutyryl have the following structures:

bz      ibu

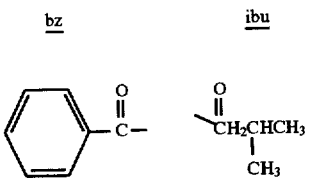

Beneficially, these protecting groups can be removed from the oligonucleotide with ammonia (i.e., "deprotected"). Additionally, ammonia can be used to remove oligonucleotides from the solid support material from which they were synthesized (i.e., "cleavage"). Advantageously, ammonia can be used as a cleavage/deprotection reagent with limited side product formation.

A practical concern exists, however, with respect to the use of ammonia as a cleavage and deprotection reagent. Ammonia requires a (relatively) long time period to complete the cleavage and deprotection process. On average, 6 minutes is required for the chemical synthesis of each nucleoside to a growing oligonucleotide; thus, for an average oligonucleotide of about 21 nucleotides (referred to as a "21-mer"), one can expect that the synthesis will require about 2 hours, using commercially available DNA synthesizers. However, approximately 24 hours (room temperature) to 6 hours (55° C.) are required for cleavage and deprotection of the oligonucleotide using ammonia. Clearly, more time is required for the final steps of cleavage and deprotection than the synthesis itself. As such, an ongoing need has existed for cleavage and deprotection reagents which can complete these steps within the same approximate order of magnitude as the synthesis itself. Such reagents are disclosed in the related application referenced above, which is incorporated herein by reference.

Broadly, such reagents comprise at least one straight chain alkylamine comprising from 1 to about 10 carbon atoms (such an alkylamine can be represented as follows: —$NH_2$ $(CH_2)_{0-10}$—$CH_3$). In a particularly preferred embodiment of the reagent disclosed in the above-referenced application, a reagent comprising methylamine and t-butylamine can be utilized to cleave and deprotect oligonucleotides in less than about 90 minutes at room temperature, and less than about 10 minutes at about 65° C.

It was observed that when these reagents are used in conjunction with oligonucleotides comprising $dC^{ibu}$ or $dC^{bz}$, the formation of an unwanted side product, N-methylcytidine, could occur. With respect to $dC^{bz}$, approximately 10% of the cytidines within the oligonucleotides were N-methylcytidine. Thus, while on the one hand a cleavage/deprotection reagent which could rapidly accomplish these tasks had been discovered, on the other hand such reagent, when used in conjunction with the so called "traditional" bz and ibu protecting groups for the base cytidine, led to cytidine side product formation.

What is needed, then, are protecting groups useful in oligonucleotide synthesis which do not have such deleterious side effects.

SUMMARY OF THE INVENTION

Disclosed herein are protecting groups which satisfy at least the above need. The disclosed protecting groups, which have the following characteristics and are thus broadly defined thereby are at least about 30 times more labile than benzoyl, and comprise a carbonyl group having a straight chain alkyl group attached thereto, the alkyl group comprising from 1 to about 10 carbon atoms, preferably from about 1 to about 6 carbon atoms, more preferably from 1 to about 3 carbon atoms, and most preferably 1 carbon atom. A particularly preferred protecting group is acetyl, represented by the following formula:

and designated herein as "Ac". Most preferably, the disclosed protecting group is used to protect cytidine bases; Ac protected deoxycytide is designated herein as "$dC^{Ac}$". The $N^4$ Acetyl deoxycytides of the present invention include but are not limited to acetyl protected deoxycytide phosphoramidites and acetyl protected deoxycytide H-phosphonates.

BRIEF DESCRIPTION OF THE DRAWINGS

The following drawings are intended to be used for purposes of illumination of the Detailed Description of Preferred Embodiments.

DETAILED DESCRIPTION OF PREFERRED EMBODIMENTS

Figure 1:
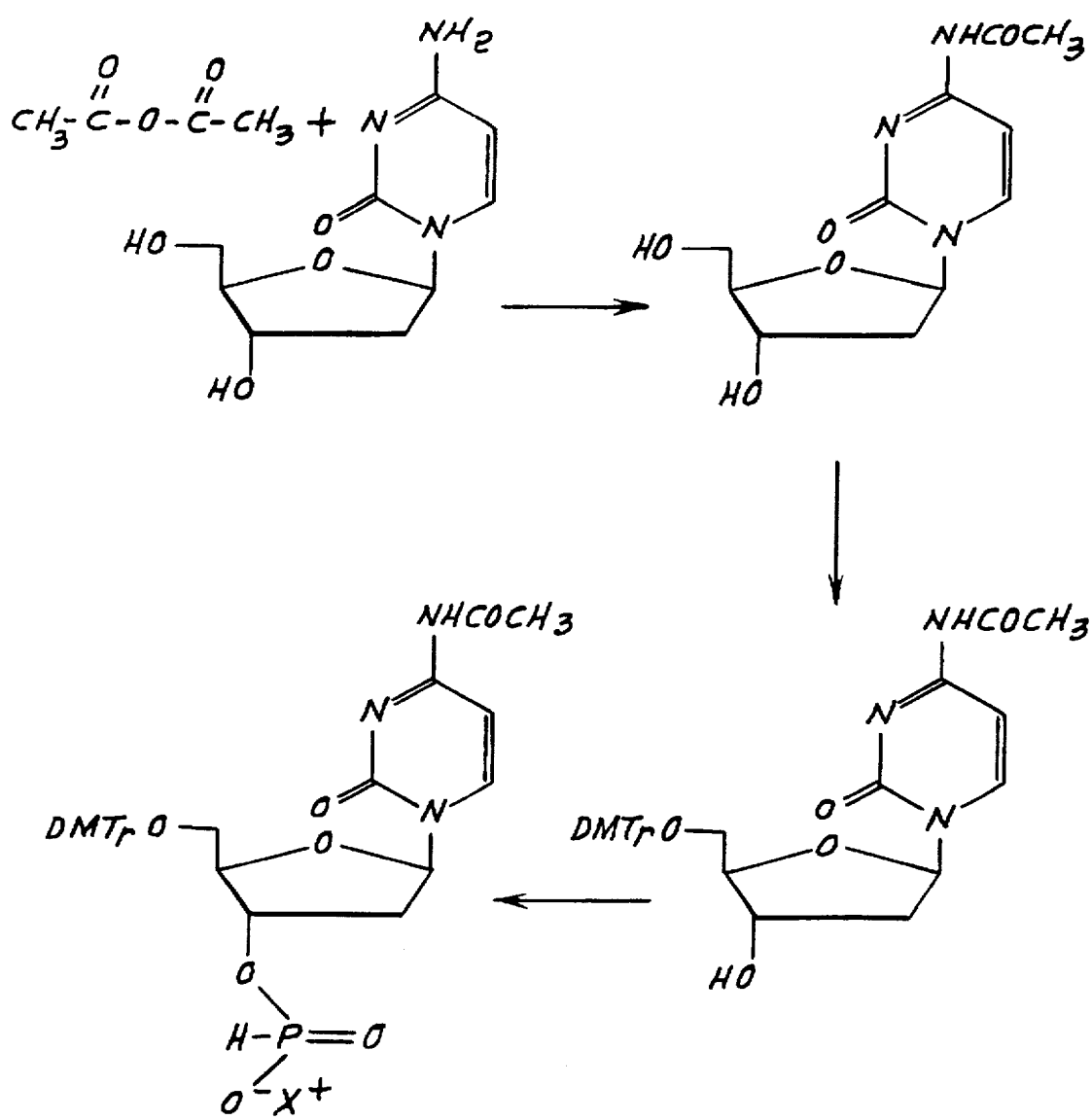
FIG. 1 is a schematic representation of the chemical synthesis disclosed in Examples I–IV.

As those in the art appreciate, the base cytidine is most susceptible to side product formation during the deprotection of oligonucleotides. Thus, by convention, it is useful to monitor side product formation of cytidine during oligonucleotide synthesis and deprotection.

During the course of investigating cleavage/deprotection reagents comprising a straight chain alkylamine having from between 1 to about 10 carbon atoms, it was discovered that oligonucleotides containing a cytidine base protected by benzoyl ("bz") or isobutyryl ("ibu") and which were subjected to such reagents had some cytidine side product formation, specifically in the form of N-methylcytidine. Accordingly, while such reagents provide the ability to rapidly cleave and deprotect oligonucleotides compared to, inter alia, ammonia, the resulting side product formation led to the need for a different protecting group for cytidine bases which would not lead to such side product formation. Such protecting groups require at least the following criteria: susceptible to deprotection comparable to bz and ibu, and not lead to the formation of statistically significant side product formation (i.e., average less than about 0.01%).

Additionally, the resulting oligonucleotide must retain, its biological activity. I.e., the oligonucleotide must be useful in terms of, complementary base pairing between, e.g., the bases C and G.

The present invention involves protecting groups useful in synthesizing oligonucleotides and oligonucleotide derivatives. The protecting groups include a carbonyl group having a straight chain alkyl group attached thereto, the alkyl group having from 1 to about 10 carbon atoms, preferably from 1 to about 6 carbon atoms, more preferably from 1 to about 3 carbon atoms, and most preferably 1 carbon atom. When the present invention is used in conjunction with a cleavage/deprotection reagent comprising at least one straight chain alkylamine having from between 1 to about 10 carbon atoms, it results in significantly reduced cytidine side product formation.

As used herein, the term "labile" means the capability of undergoing a chemical change. The protecting groups utilized in the compounds and compositions of the present invention can be represented as follows:

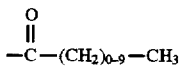

As used herein, the term "oligonucleotide" is meant to encompass synthetic oligonucleotide as well as oligonucleotide derivates or modified oligonucleotides, i.e. where the 3' end, 5' end, sugar, or heterocyclic base are modified, as well as modification of the phosphate backbone (e.g. methyl phosphonates, phosphorothioates, and phosphoramidates). Additionally, oligonucleotides can include oligonucleotides having an attached reporter group, e.g. biotin, avidin, haptens, dyes, fluorescent, chemiluminescent, enzymatic or radioactive labels, and solid supports other than the solid support from which the oligonucleotide is synthesized.

A particularly preferred protecting group in accordance with the disclosure is acetyl, represented as follows:

and referenced herein as "Ac". Preferred embodiments of the present invention are deoxycytidine compounds protected with acetyl (designated herein as "$dC^{Ac}$"). Contemplated within this invention are $N^4$ acetyl deoxycytidine compounds useful in preparing oligonucleotides, modified oligonucleotides, and oligonucleotide derivatives including DNA derivatives and RNA derivatives. In particular, such compounds include deoxycytidine phosphoramidites protected at the $N^4$ position with any of the foregoing protecting groups and deoxycytidine H-phosphonates similarly protected at the $N^4$ position. The protected deoxycytidine H-phosphonates of the present invention have the following general formula:

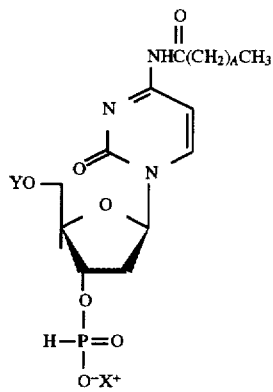

wherein A is an integer having a value of from 0–9, X is a counterion, and Y is selected from the group consisting of hydrogen, trityl protecting group, and a pixyl protecting group.

In preferred embodiments A, is 0, X is a quaternary amine, and Y is dimethoxytrityl (DMT). As will become evident in the discussion below, the nature of the counterion depends upon the quencher utilized in the reaction to prepare the deoxycytidine H-phosphonate. Typically, a tertiary amine is used to quench the reaction, making the counterion a quaternary amine.

Like phosphoramidities, the H-phosphonates of the present invention are particularly useful in the synthesis of oligonucleotides for diagnostic and therapeutic applications. While phosphoramidites are generally the preferred reagents for the synthesis of high quality longer oligonucleotides (e.g. longer than about 100 bases), H-phosphonates are frequently the reagent of choice for the synthesis of shorter oligomeric nucleotides. This is because the quality of shorter oligonucleotides prepared with H-phosphonate reagents is good and the H-phosphonate reagents are less prone to oxidation than their phosphoramidite counterparts, making their handling easier and less critical.

Accordingly, the ability to prepare oligonucleotides using H-phosphonate reagents and deprotect the synthesized oligonucleotides with little or no side product formation is highly desirable. The protected H-phosphonates described herein provide this advantage.

Preparing the deoxycytidine H-phosphonates of the present invention involve first protecting deoxcytidine at the $N^4$ position by reacting deoxycytidine in a suitable solvent with an active reagent such as acetic anhydride. The resulting $N^4$ protected deoxycytidine is then protected at the 5' position with a suitable protecting reagent such as DMT using methods known in the art.

The H-phosphonate of the suitably protected deoxycytidine can be prepared by reacting the protected deoxycytidine in a $PCl_3$/imidazole mixture. At the completion of the reaction, the reaction is quenched, typically with a tertiary amine to form a $N^4$ acetyl deoxycytidine H-phosphonate suitable for using in the synthesis of oligonucleotides. The protected H-phosphonate deoxycytidines are suitable for use in any reaction system used to prepare oligonucleotides, modified oligonucleotides or polynucleotides, including automated nucleotide synthesizers. That is, the $N^4$ protected deoxycytidines of the present invention can be used in place of prior art deoxycytidine reactants in the synthesis of oligonucleotides. The $N^4$ protected deoxycytidines of the present invention are equally applicable in the synthesis of modified oligonucleotides including phosphothioate based modified oligonucleotides. These modified oligonucleotides are prepared typically by utilizing a sulfurizing step during the oxidation step of standard oligonucleotide synthesis.

While not wishing to be bound to any particular theory, it is believed that the relative lability of bz versus ibu is responsible for an increase in cytidine side product formation in the presence of an alkylamine cleavage/deprotection reagent. Ibu is (relatively) more labile than bz; in the presence of an alkylamine, oligonucleotides containing cytidine base protected with ibu led to less percentage of N-methylcytidine side product formation than comparative oligonucleotides containing cytidine protected with bz. Accordingly, it was postulated that chemical moieties which could function as protecting groups and which were more labile than bz might evidence statistically less cytidine side product formation. It was further postulated that lability is affected by the electronic donation of the groups adjacent to the carbonyl group, I.e., as the electronic donation increases, the carbonyl carbon becomes less electropositive and hence less susceptible to nucleophilic attack by the deprotection reagent. For example, the electron donation from the secondary (i.e., branched) carbons to the carbonyl carbon of ibu is greater than the donation from the primary carbon to the carbonyl carbon of Ac.

Acetyl is significantly more labile than ibu and, additionally, is the least "bulky" of the disclosed, defined protecting groups. Acetyl can be readily conjugated to the exocyclic amino group of the cytidine base, and, as determined experimentally, can be efficiently and effectively utilized in conjunction with inter alia, alkylamine cleavage/ deprotection reagents without statistically significant side-product formation.

EXAMPLES

The following Examples, directed to preferred embodiments of the invention are not intended, nor should they be construed that be, limitations on the disclosure or the claims that follow:

I. Materials and Methods

A. Reagents

1. Cleavage/Deprotection Reagent

All chemicals were at least of ACS grade. Ammonium hydroxide was obtained from Aldrich (Milwaukee, Wis.; Cat. No. 22, 122-8). Methylamine, 40 wt % solution in water, was obtained from Aldrich (Cat. No. M2, 775-1), as was t-butylamine (Cat. No. B8, 920-5).

Methylamine/t-butylamine reagent was prepared by mixing a 1:1 volume-to-volume ratio, followed by shaking for 5 minutes at room temperature and storage at 4° C. Ammonium hydroxide was stored in accordance with supplier instructions.

2. Protected Deoxynucleosides

The following protected deoxynucleosides were obtained from Sigma Chemical Co. (St. Louis, Mo.):

a) $dA^{bz}$ (Cat. No. B 6130);

b) $dC^{bz}$ (Cat. No. B 5882);

c) $dC^{ibu}$ (Cat. No. I 6261); and d) $dG^{ibu}$ (Cat. No. I 6007).

Thymidine was obtained from Sigma (Cat. No. T 5018).

B. Commercially Available Protocols

1. Polymerase Chain Reaction ("PCR")

PCR analysis of oligonucleotide primers subjected to the disclosed cleavage/deprotection reagent was conducted using a Perkin Elmer Cetus GeneAmp™ DNA Amplification Reagent Kit with AmpliTaq™ (Part NO. N801-0055). Manufacturer instructions were followed.

2. DNA Sequencing

Sequencing reaction was performed using M13mp18 single stranded DNA template (New England Biolabs, Cat. No. 404-C) following the protocol of United States Biochemical Sequenase® Version 1.0, using $\alpha$-[$^{35}$S]-dATP.

C. Instruments

1. Automated DNA Synthesizer

Synthesis of oligonucleotides was performed using a Biosearch 8750™ DNA synthesizer; controlled pore glass (CPG), 500 Å–1000 Å pore size, was used for the solid support material. Homo- and hetero-oligonucleotides of various lengths were synthesized in accordance with manufacturer instructions.

2. Capillary Electrophoresis

Capillary electrophoresis of oligonucleotides was performed on a Beckman Instruments, Inc. P/ACE™ 2000 high performance capillary electrophoresis system. A 37 cm U100P Urea Gel Column (Beckman, Cat. No. 338480) was utilized. Samples were loaded onto the columns via the electrokinetic injection method (10 kV, 3 seconds); separation was conducted at 11 kV/cm for 30–90 minutes, depending on oligonucleotide length. Tris-hydroxymethyl aminomethane ("TRIS")-borate 7M urea running buffer (Beckman, Gel Buffer Kit, Cat. No. 338481) was utilized. Absorbance detection was in the range of from 0.05 to 2.0 $OD_{260\ nm}$/ml, depending principally on the length of the oligonucleotide.

3. High Pressure Liquid Chromatography ("HPLC")

HPLC analysis was conducted on a Beckman Instruments System Gold™ HPLC Programmable Solvent Module 126 equipped with a diode array detector module 168 and autosampler 507. A $C_{18}$ Ultrasphere™ HPLC column (Beckman, Cat. No. 235329; 5µ particles, 4.6 mm×25 cm) was utilized. Bottle A contained 0.1M ammonium acetate, pH 6.9; Bottle B contained HPLC-grade acetonitrile. The system was operated in a gradient mode as follows (1 ml/min. flow rate): 0–10 min: 85% Bottle A, 15% Bottle B; 20–25 min: 75% Bottle A, 25% Bottle B; 25–27 min: 50% Bottle A, 50% Bottle B; 27–30 min: 50% Bottle A, 50% Bottle B; 30–35 min, 100% Bottle A, 0% Bottle B.

II.

EXAMPLE I

Preparation of 2' Deoxycytidine

A suspension of 71 g (269.3 mmol) of 2'-deoxycytidine—hydrochloric acid (Pennisula, Belmont, Calif.; Cat. No. N1012) and 1600 ml methylene chloride was admixed with 42 ml (301 mmol) triethylamine (Aldrich; Cat. No. 206-3). The admixture was vigorously stirred at ambient temperature for 4 hrs. A colorless, crystalline solid was collected, washed with methylene chloride (3×80 ml) and air dried. 61g (99% yield) of a material having a melting point within the range of 185°–195° C. was obtained; the published melting point of free base 2-deoxycytidine is 185°–195° C.

EXAMPLE II

Preparation of $N^4$-Acetyl-2'Deoxycytidine

To 61.29 g (270 mmol) of the material of Example I dissolved in 1300 ml of anhydrous N,N-dimethylformamide ("DMF") (Aldrich; Cat. No. 22, 70506), was added 28 ml (296 mmol) of acetic anhydride (Aldrich; Cat. No. 11,004-3), and the resulting mixture was stirred at room temperature for 20 hrs. DMF was removed under reduced pressure, and the resulting residue was treated with the excess of 100 ml dimethyl ether; 71.4 g (98% yield) of a crystalline product was obtained and collected by filtration, washed thoroughly with dimethyl ether, and dried over $P_2O_5$ for 3 hrs. This product had a melting point of 150°–170° C.; the published melting point for this product 154°–176° C.

The calculated compositional molecular weight for $N^4$-acetyl-2'-deoxycytidine-$H_2O$ ($C_{11}H_{15}N_3O_5$—$H_2O$) is: C-45.99; H-5.97; and N-14.63. The crystalline product had the following compositional molecular formula as determined by elemental analysis: C-45.71; H-6.10; and N-14.38. It was further determined by infra-red spectra that the crystalline product contained a single carbonyl amide moiety and a single carbonyl ring amide. The structure was further confirmed by nuclear magnetic resonance ("NMR"). The foregoing is consistent with the structure of $N^4$-acetyl-2'-deoxycytidine.

EXAMPLE III

Preparation of $N^4$-Acetyl-5'-O-(4,4'-dimethoxy-trityl)-2'-Dexoycytidine 70 g (260.2 mmol) of the product of Example II was dried by co-evaporation with 2×50 ml dry pyridine (Aldrich; Cat. No. 27,097-0), then taken up in 1300 ml of dry pyridine, ice-cooled; thereafter, 105 g (314 mmol) of 4,4'-dimethoxy-trityl chloride ("DMTr-Cl") Peninsula; Cat. No. N4011) was added to the solution. The mixture was left stirring at 5° C. for 20 hrs. Pyridine was removed under reduced pressure, and the resulting residue was taken up in 3.0 liters of methylene chloride, washed with 2×2 liters of 5% sodium hydrogen carbonate (Aldrich; Cat. No. 23,931-3) and 1×2 liters of deionized water. The organic layer was dried over sodium sulfate and concentrated to near dryness. The product was purified on a 6×80 cm silica gel column (Aldrich; 70–230 mesh; Cat. No. 28,864-4) by gradient elution with 20.0 liters 0–6% methylene-chloride-methanol. Desired fractions were collected, concentrated to approximately 300 ml, and added drop-wise to 3.0 liters cooled (0° C.) hexane (Baxter, McGaw Port, Ill.; Cat. No. 216-4 DK) to precipitate the product. The precipitated product was filtered, washed with hexane and air dried to yield 117 g (79% yield) of a product.

The calculated compositional molecular weight for $N^4$-acetyl-5'-O-(4,4'-dimethoxy-trityl)-2'deoxycytidine ($C_{32}H_{33}N_3O_7$) is: C-67.24; H-5.82; and N-7.35. The product had the following compositional molecular formula as determined by elemental analysis: C-66.02, H-6.05; and N-6.91. It was further determined by infra-red spectra that the crystalline product contained a single carbonyl amide moiety and a single carbonyl ring amide. The structure was further confirmed by NMR. The foregoing is consistent with the structure of $N^4$-acetyl-5'-O-(4,4'-dimethoxy-trityl)-2'-deoxycytidine.

EXAMPLE IV

Preparation of $N^4$-Acetyl-5'-O-(4,4'-dimethoxy-trityl)-2'-deoxycytidine-3'-O (N,N-diisopropyl)-β-cyanoethyl-phosphoramidite 11.44 g (20 mmol) of the product of Example III was dried by successive co-evaporation with pyridine, toluene and tetrahydrofuran ("THF") (Aldrich; Cat. No. 18,656-2), refluxed and distilled over $CaH_2$. The dried residue was dissolved in 100 ml of dry THF and 14 ml (80 mmol) of N,N,N-diisopropylethylamine was added thereto. This was followed by 5 min drop-wise addition (via a syringe) of 8.92 ml (40 mmol) β-cyanoethylmonochloro-N,N-diisopropyl phosphoramidite with constant stirring under argon at room temperature. After 60 min of stirring, 1.2 ml of methanol (40 mmol) was added to the mixture, and stirring was continued for another 60 min, and evaporated to dryness. The residue was dissolved in 600 ml ethylacetate (Baxter; Cat. No. CP80132-4DK), washed with 10% $NaHCO_3$ (2×500 ml) and dried over $Na_2SO_4$. The organic layer was evaporated and the residue was dissolved in 50 ml ether; this was then added by drop-wise addition to 700 ml of hexane at room temperature. The mixture was decanted, and the precipitated product was dissolved in 100 ml ether, followed by the addition of 700 ml of hexane and stirring at room temperature. This mixture was decanted and the product dissolved in 500 ml $CH_2Cl_2$, followed by the addition of 30 g basic alumina (Aldrich; Cat. No. 19,944-3) and stirring for 1 hr at room temperature. The mixture was filtered in a sintered glass funnel, evaporated and dried in a desiccator over $CaCl_2$, $P_2O_5$ under reduced pressure. 11 g (76% yield) of a product was obtained; as determined by reverse-phase HPLC, the purity thereof was 98.4%.

The calculated compositional molecular weight for $N^4$-acetyl-5'-O-(4,4'-dimethoxy-trityl)-2'-deoxycytidine-3'-O-(N,N-diisopropyl)-β-cyanoethyl-phosphoramidite ($C_{41}H_{50}N_5O_8P$) is: C-63.80; H-6.53; N-9.07; and P-4.01. The compositional molecular formula of the product, as determined by elemental analysis, was: C-62.51; H-6.84; N-8.68, and P-3.61. It was further determined by infra-red spectra that this product contained a single carbonyl amide moiety, a single carbonyl ring amide and a single —C≡N group. The structure was further confirmed by NMR. The foregoing is consistent with the structure of $N^4$-acetyl-5'-O-(4,4'-dimethoxy-trityl)-2'-deoxycytidine-3'-O-(N,N-diisopropyl)-β-cyanoethyl-phosphoramidite.

The product in Example IV was designated "$dC^{Ac}$" as indicating a deoxycytidine comprising an acetyl protecting group. A schematic diagram outlining the preparation steps of Examples I–IV is set forth in FIG. 1.

EXAMPLE V

Cytidine Side Product Formation

As noted, deoxycytidine is ordinarily most susceptible to side product formation during deprotection of oligonucleotides comprising deoxycytidine. Typically, such side product formation is via transamination.

As those in the art appreciate, the synthesis of oligonucleotides is typically conducted with the intent of retrieving the end-product as quickly as possible. Occasionally, however, it is possible that the solubilized, deprotected oligonucleotide may remain in a deprotection reagent for extended time periods. As those in the art further appreciate, such an increase in time when the oligonucleotide is within the reagent can increase the chance of a transamination event, thus increasing the chance of side product formation.

Cytidine side product formation was investigated by reverse phase HPLC, using both methylamine and methylamine/t-butylamine as the reagent, across several times and temperatures. The "traditional" cytidine protecting groups, "bz" and "ibu" were studied, as well as an acetyl protecting group. The side product observed when utilizing such reagent (as confirmed by Nuclear Magnetic Resonance) was N-methyl cytidine. Percentage of N-methyldeoxycytidine formation, relative to deoxycytidine, are presented below, based upon solution-based deprotection of deoxycytidine protected with an acetyl protecting group:

TABLE I

Percentage of N-methylcytidine Formation*

| Reagent | TEMPERATURE | | |
|---|---|---|---|
| | 25° C. | 37° C. | 65° C. |
| Methylamine | <0.01** (60 min.) | <0.01 (20 min.) | <0.01 (5 min.) |
| Methylamine (16 hrs.) | ~0.05 | ~0.25 | ~2.5 |
| Methylamine/ t-butylamine (16 hrs.) | <0.01 | <0.01 | ~0.6% |

*average percentages
**0.01% is the lowest detectable limit of the instrument

These results indicate that for a typical oligonucleotide synthesis (i.e. one in which the investigator is desirous of obtaining the finished end product as soon as possible), the methylamine does not lead to statistically significant cytidine side product formation. However, as the time that the oligonucleotide remains in the reagent increases, so too does the formation of cytidine side product formation. Thus, the use of a Transamination Suppression Reagent ("TSA") is useful. A "TSA" is defined herein as an agent useful in the suppression of transamination, i.e. the exchange of amines on a nucleotide, typically manifested as side-product formation. Preferably, the TSA is an agent (or agents) having a polarity index value that is at least 1.5 times less than that for water, preferably selected from the group consisting of straight chain, branched, cyclic, saturated and unsaturated alkylamines having from between 1 and about 10 carbon atoms and which may further comprise functional groups; ethanol; methanol; isopropylamine; acetyl nitrile; dimethylformamamide; tetrahydrofuran; and combinations of the foregoing. Exemplary alkylamines as defined include, but are not limited to, t-butylamine, ethylamine, propylamine, isopropylamine, dimethylamine, diethylamine, trimethylamine and secondary butylamine. The data indicates that relative to methylamine, a reagent comprising methylamine and t-butylamine as a TSA significantly reduces cytidine side product formation.

A secondary set of studies was conducted along these lines. For these studies, side product formation for $dC^{Ac}$, $dC^{ibu}$, $dC^{bz}$, $dG^{ibu}$, $dA^{bz}$ and dT (as a relative percentage of non-side product formation for the nucleosides) were investigated at various times and temperatures using methylamine/t-butylamine as the reagent. Results are as presented in Table II:

TABLE II

Percentage of Side Product Formation*

| Temp. (°C.) | Reaction Time | $C^{AC}$ | $C^{ibu}$ | $C^{ibz}$ | $G^{ibu}$ | $A^{bz}$ | T |
|---|---|---|---|---|---|---|---|
| 25 | 90 min. | ** | 0.15 | 10.0 | ** | ** | ** |
| 25 | 16 hrs. | ** | *** | *** | ** | ** | ** |
| 37 | 30 min. | ** | 0.15 | 10.0 | ** | ** | ** |
| 37 | 5 hrs. | ** | *** | *** | ** | ** | ** |
| 37 | 16 hrs. | ** | *** | *** | ** | ** | ** |
| 65 | 5 min. | ** | 0.15 | 10.0 | ** | ** | ** |
| 65 | 1 hr. | ** | *** | *** | ** | ** | ** |
| 65 | 16 hrs. | 0.6 | *** | *** | ** | ** | ** |
| 80 | 3 min. | ** | 0.15 | 10.0 | ** | ** | ** |
| 80 | 1 hr. | *** | *** | ** | ** | ** | ** |

*Averages
**<0.01
***no investigated due to high percentages at optimal temperature/reaction time These results indicate at least several things. First, with respect to the dC protection groups, the data indicates that acetyl protecting groups provide superior results when used in conjunction with the straight chain alkylamine cleaving and deprotecting reagent; the "traditional" cytidine protecting groups resulted in significantly higher side product formation. Second, this deprotecting and cleaving reagent does not lead to statistically significant side product formation for any of the protected deoxynucleosides at any of the investigated temperatures or reaction times, with the exception of deprotection of $dC^{Ac}$ at the elevated temperatures and at times greater than the desired reaction times. Thus, for oligonucleotides comprising deoxycytidine protected with an acetyl protecting group, it is preferred that at such elevated temperatures, extended reaction times not be utilized.

EXAMPLE VI

Enzymatic Digestion Analysis of Non-Purified Oligonucleotides

Analysis of the composition of several oligonucleotides were conducted using enzymatic digestion and reverse phase HPLC techniques. These studies were conducted using deoxycytidines protected with an acetyl protecting group and a traditional protecting group, bz; all other protecting groups were consistent between the oligonucleotides. 35-mers, 51-mers and 101-mers, having the following sequences, where analyzed:

35-mer
5'-CAG—TGC—AGC—TCC—TAG—CAG—CCT—AGC—GTA—CTA—GTC—TT-3'

51-mer
5'-CAG—TCC—TAG—TCA—CAG—TCC—AGT—CGC—TCA—AGC—GTC—CAG—
TTG—CAC—AGG—TCA—CCT-3'

101-mer
5'-GCT—GCC—AGT—TCG—GTC—ATC—CGA—TCC—TCG—GTC—ACG—CAA—
CTG—TCA—ACG—GCA—CCT—ACT—CCT—CGT—AAC—GTA—GGA—CAG—TCC—
GAT—TCG—C4C—GTG—CAA—AGC—CCA—TTC—AT-3'

The oligonucleotides were cleaved and deprotected using a reagent comprising methylamine/t-butylamine at 25° C. for 90 minutes or ammonia for 3 hrs. at 65° C.; solubilized, deprotected oligonucleotides were not purified prior to analysis. Results are as follows in Table III:

TABLE III

| | | | Composition Analysis | |
|---|---|---|---|---|
| | | | Determined | |
| | | Theoretical | Oligonucleotides Comprising dC$^{Ac}$ | Oligonucleotides Comprising dC$^{bz}$ |
| 35-mer | C | 11 | 10.67 | 10.62 |
| | G | 8 | 7.88 | 7.84 |
| | T | 9 | 9.65 | 9.41 |
| | A | 7 | 6.80 | 7.13 |
| 51-mer | C | 18 | 17.04 | 17.36 |
| | G | 11 | 11.71 | 11.72 |
| | T | 11 | 11.61 | 11.07 |
| | A | 11 | 10.65 | 10.85 |
| 101-mer | C | 35 | 33.80 | 33.53 |
| | G | 22 | 20.74 | 20.70 |
| | T | 22 | 21.78 | 21.73 |
| | A | 22 | 25.09 | 25.04 |

The theoretical composition of the various non-purified oligonucleotides and the determined composition provide good correlation. Additionally, the difference in deoxycytidine protecting groups, based upon the above data, does not indicate a statistically significant difference in results.

EXAMPLE VII

DNA Sequencing

Two sets of 18-mers were synthesized using an acetyl protecting group for deoxycytide and, for comparative purposes, bz, and were subjected to a reagent comprising methylamine/t-butylamine for 90 min. at 25° C., and ammonia for 3 hrs. at 65° C., respectively. The 18-mers had the following sequence:

18-mer

5'-CGC-CAG-GGT-TTT-CCC-AGT-3'

Solubilized, deprotected oligomers were purified using Sep Pak (Waters, Part no. 5190) DNA purification kit. These purified oligomers were used as primers for sequencing purposes. The template was M13mp18 single stranded DNA (New England Biolabs, Cat. No. 404-C); sequencing was accomplished using the 18-mers in conjunction with, the USB Sequenase materials and protocols. Results are presented in FIG. 2.

Figure 2:
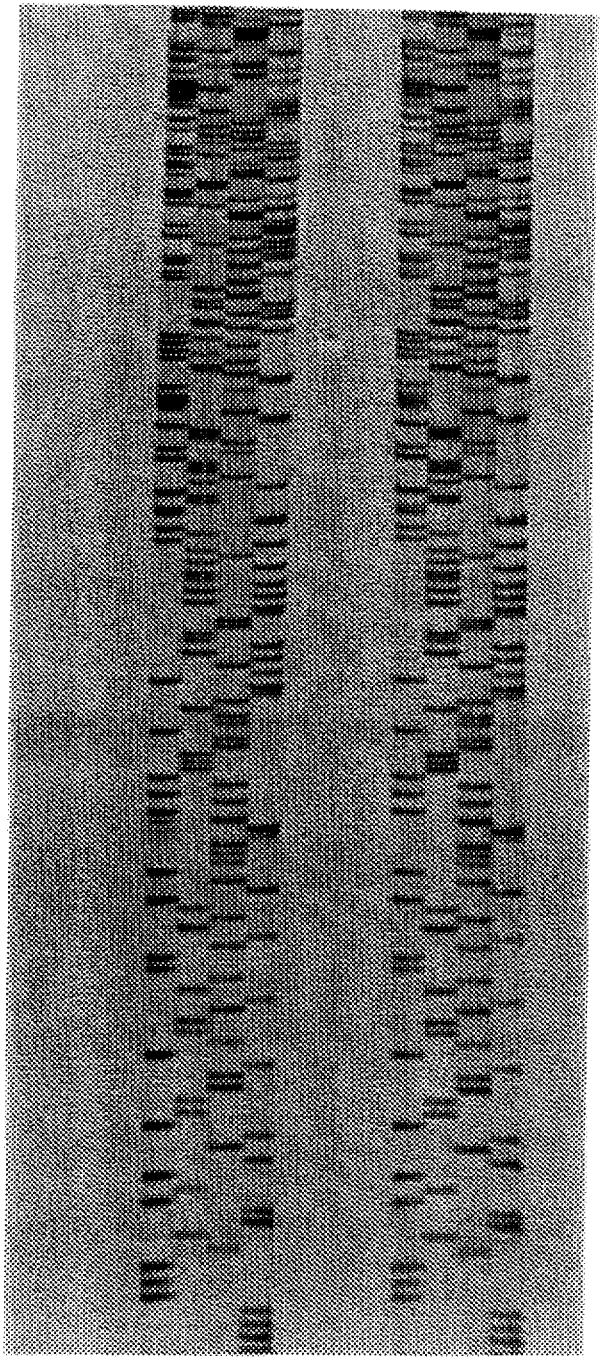
FIG. 2 is a photographic reproduction of a sequencing reaction of the template M13mp18.

As the results of FIG. 2 indicate, the sequencing band patterns are substantially identical using primers subjected to a methylamine/t-butylamine reagent and acetyl protecting group vis-a-vis primers derived via ammonia and bz.

EXAMPLE VIII

Preparation of N$^4$ acetyl 2' deoxycytidine H-Phosphonate

The following describes a method for the preparation of an N$^4$ acetyl deoxycytidine H-phosphonate according to the following general procedure:

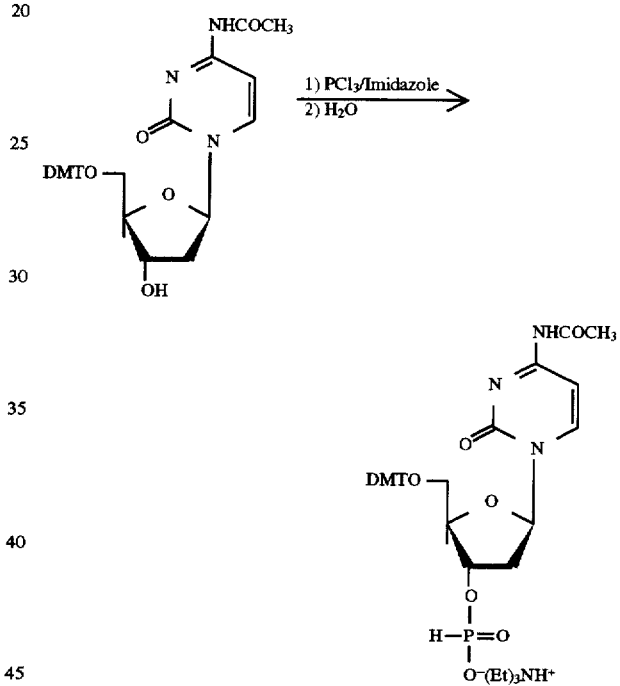

A portion of imidazole (3.6 grams or 53 moles) was dissolved in 100 mL of acetonitrile and after cooling to 0° C. 1.4 mL or 16 moles of PCl$_3$ and 7.8 mL of triethylamine were added to the acetonitrile. The acetonitrile mixture was stirred for 30 minutes and then 2.11 grams (3.7 moles) of 5' DMT N$^4$-acetyl deoxycytidine prepared as in Examples II and III was added to the acetonitrile mixture dropwise over a 30 minute period. The resulting acetonitrile reaction mixture was stirred for 4 hours at room temperature. Then 25 mL of water was added to the reaction mixture and the stirring was continued for an additional 30 minutes. The resulting solution was evaporated and then coevaporated with a pyridine/triethylamine (4:1 v/v) solution by using 2×50 mL portions of the pyridine/triethylamine solution. The resulting residue was dissolved in 200 mL of CHCl$_3$, washed with 200 mL of water and dried over Na$_2$SO$_4$. This mixture was filtered and evaporated. The solid residue was redissolved in 10 mL of CHCl$_3$ and then precipitated with 500 mL of ether. The resulting solid was filtered, washed with ether and dried to provide 1.8 g (66% yield) of the acetyl protected deoxycytidine H-phosphonate.

The product was characterized by melting point and was found to decompose upon melting between 130°–145° C. The H-phosphonate product was evaluated using proton NMR and $^{31}$P-NMR and found to have the following absorptions:

$^1$H-NMR (CDCl$_3$)δ1.29 (t, 3H, NCH$_2$CH$_3$) ,2.18 (s, 3H, CO CH$_3$) , and 2.72 (2m, 2H, C$_2$, CH$_2$), 3.05 (q, 2H, N CH$_2$ CH$_3$), 3.48 (m, 2H, C$_5$, CH$_2$), 3.78 (s, 6H, 2×O CH$_3$), 4.22 (m, 1H, C4, H), 5.03 (m, 1H, C$_3$, H), 6.21 (t, 1H, C$_1$, H), 6.90 (d, 1H, JpH+600 Hz, H-P), 6.83–7.40 (m, 14H, C$_6$H and DMT aromatic protons), 8.29 (d, 1H, C$_6$H), and 10.34 (br, s, 1H, NHCO).

$^{31}$P-NMR (CDCl$_3$): δ4.16 ppm and −0.99 ppm JH-P+ 625.95 Hz

The acetyl protected deoxycytidine synthesized according to the foregoing procedure was analyzed using HPLC and found to have a purity of 100%.

EXAMPLE IX

Synthesis of oligonucleotides utilizing the H-phosphonate prepared in Example XIII The N$^4$ acetyl deoxycytidine H-phosphonate prepared in Example XIII was used to prepare a 21-mer and a 25-mer using a Biosearch automated DNA synthesizer. The procedure used was according to manufacturer directions except that instead of N$^4$ benzoyl deoxycytidine H-phosphonate the N$^4$ acetyl deoxycytidine H-phosphonate prepared according to Example VIII above was used. The resulting 21-mer and 25-mer each had the quality of olignucleotides prepared using a conventional C$_{bz}$ H-phosphonate. Also, the deprotection and cleavage reactions proceeded in the same manner as described in Example 5 with no or negligible side products.

While the foregoing has been described in considerable detail, it is to be understood that the embodiments disclosed in the Detailed Description and Examples are not to be construed as limiting to the disclosure or the claims to follow. The invention is not limited to automated DNA synthesizers. The invention is not limited to deoxyribonucleic acid oligonucleotides, but can also be utilized with ribonucleic acid oligonucleotides. The invention is not limited to the use of the disclosed protecting groups only with respect to the base cytosine. The invention is not limited to use in conjunction with the specific embodiment of the reagent disclosed in the referenced co-pending application, but rather is intended to be utilized in conjunction with inter alia, the reagents broadly disclosed and claimed therein. Modifications and changes that are within the purview of those skilled in the art are intended to fall within the scope of the following claims.

---

What is claimed is:

1. A compound having the following structure:

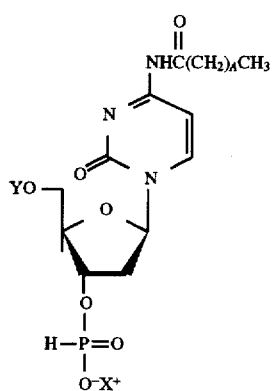

wherein A is an integer having a value of from 0–9, X is a counterion, and Y is selected from the group consisting of hydrogen, a trityl protecting group, and a pixyl protecting group.

2. The compound of claim 1 wherein A is a whole number between 0 and 5.

3. The compound of claim 1 wherein the counterion is a quaternary amine functionality.

4. A compound having the following structure:

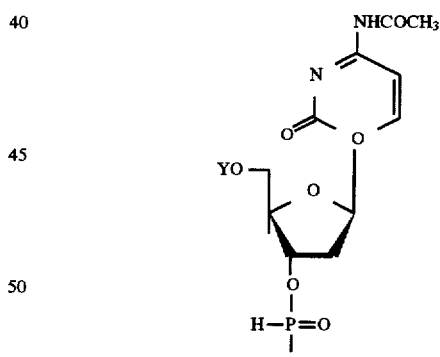

wherein X is a counterion, and Y is selected from the group consisting of hydrogen, a trityl protecting group, and a pixyl protecting group.

5. The compound of claim 4 wherein the counterion is a quaternary amine functionality.

6. An improved process for preparing oligonucleotides and modified oligonucleotides including the addition of deoxycytidine derivatives to form deoxycytidine containing oligonucleotides; the improvement which comprises utilizing a protected deoxycytidine derivative having the formula:

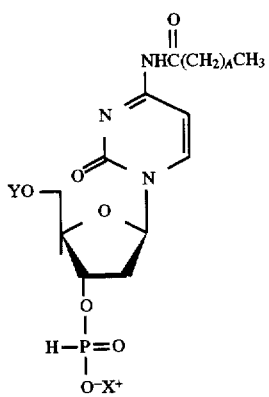
wherein A is an integer having a value of from 0–9, X is a counterion, and Y is selected from the group consisting of hydrogen, a trityl protecting group, and a pixyl protecting group.
7. The process of claim 6 wherein A is a whole number between 0 and 5.
8. The process of claim 6 wherein A is 0.
9. The process of claim 6 wherein the counterion is a quaternary amine functionality.
* * * * *